United States Patent [19]
Julian

[11] Patent Number: 5,489,225
[45] Date of Patent: Feb. 6, 1996

[54] ELECTRICAL TERMINAL WITH A COLLET GRIP FOR A DEFIBRILLATOR

[75] Inventor: Chris A. Julian, Sunnyvale, Calif.

[73] Assignee: Ventritex, Inc., Sunnyvale, Calif.

[21] Appl. No.: 168,889

[22] Filed: Dec. 16, 1993

[51] Int. Cl.⁶ ...................................................... A61N 1/02
[52] U.S. Cl. .............................. 439/837; 279/51; 607/36; 607/116
[58] Field of Search ..................................... 439/837, 836, 439/835; 279/46.3, 46.9, 51; 409/233; 607/36, 116

[56] References Cited

U.S. PATENT DOCUMENTS

| 1,667,485 | 4/1928 | Macdonald | 439/836 |
|---|---|---|---|
| 2,438,797 | 3/1948 | Bagge | 279/51 |
| 2,845,898 | 8/1958 | Stanek | 279/46.3 X |
| 3,760,332 | 9/1973 | Berkovits et al. | 339/66 R |
| 4,171,821 | 10/1979 | Miller | 279/46.9 X |
| 4,540,236 | 9/1985 | Peers-Trevarton | 439/268 |
| 4,784,141 | 11/1988 | Peers-Trevarton | 128/419 |
| 5,069,209 | 12/1991 | Posin | 129/149 |
| 5,076,270 | 12/1991 | Stutz, Jr. | 607/37 |
| 5,118,229 | 6/1992 | Lyons et al. | 409/233 X |
| 5,252,090 | 10/1993 | Giurtino et al. | 439/441 |
| 5,261,395 | 11/1993 | Oleen et al. | 607/45 |

FOREIGN PATENT DOCUMENTS

| 0414469 | 9/1910 | France | 439/839 |
|---|---|---|---|
| 0414659 | 1/1947 | Italy | 439/839 |
| 0414115 | 7/1934 | United Kingdom | 439/839 |

OTHER PUBLICATIONS

"Cardiac Difibrillators—Connector Assembly for Implantable Defibrillators—dimensional and Test Requirements" International Standard, ISO 11318:1993(E).
"Cardiac Pacemakers—Part 3: Low–profile Connectors (IS–1) for Implantable Pacemakers" Internation Standard ISO 5841-3, First Edition, 1992-12-01.

Primary Examiner—Neil Abrams
Attorney, Agent, or Firm—Steven M. Mitchell; M. Elizabeth Bush; Mark J. Meltzer

[57] ABSTRACT

A terminal for detachably connecting an electrical lead connector pin to an electrical device is disclosed. The terminal includes an outer sleeve and a movable collet for movement between first and second positions relative to the outer sleeve. The collet has a plurality of fingers thereon that are movable relatively toward and away from one another between a first spaced apart position less than the diameter of the electrical lead connector pin and a second spaced apart position greater than the diameter of the electrical lead connector pin for receiving and releasing the lead in the second spaced apart position and for gripping the lead in the first spaced apart position. The terminal further includes a spring and a push button release means for moving the collet between its first and second positions.

18 Claims, 6 Drawing Sheets

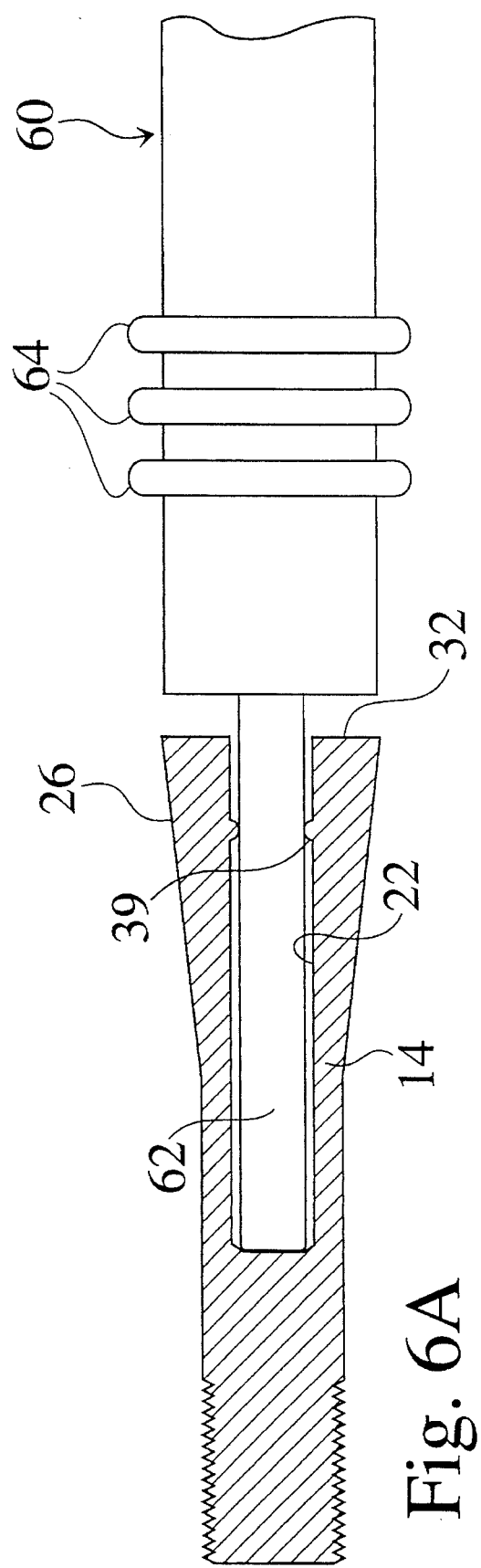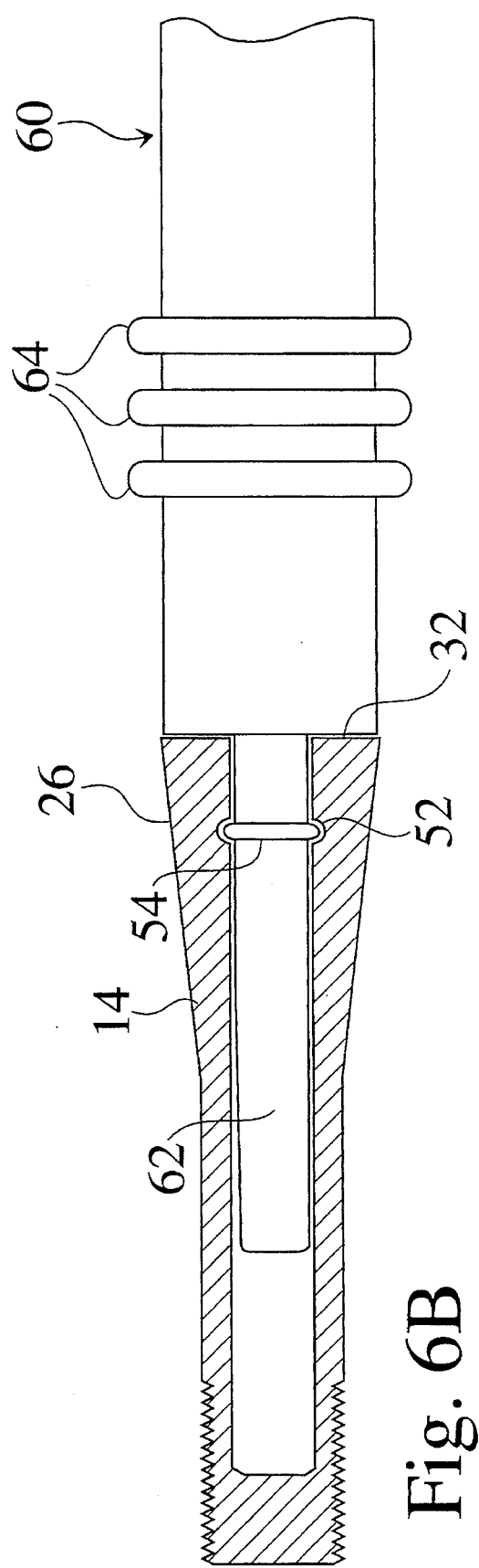

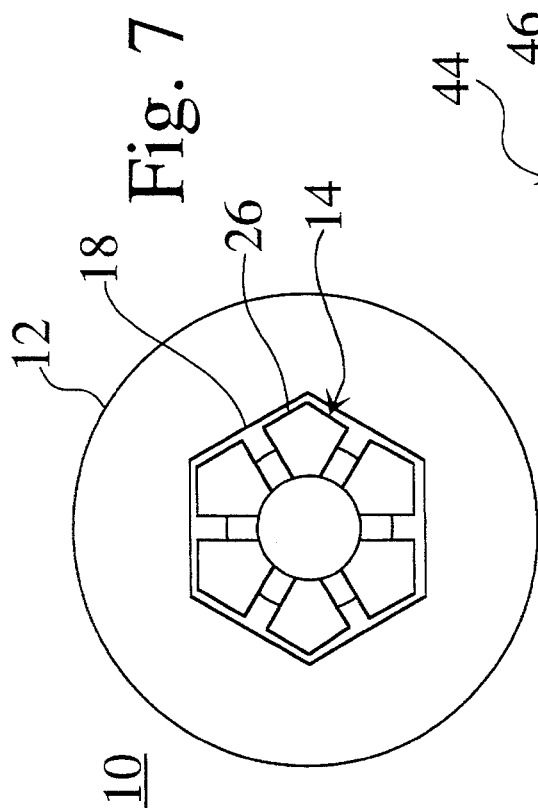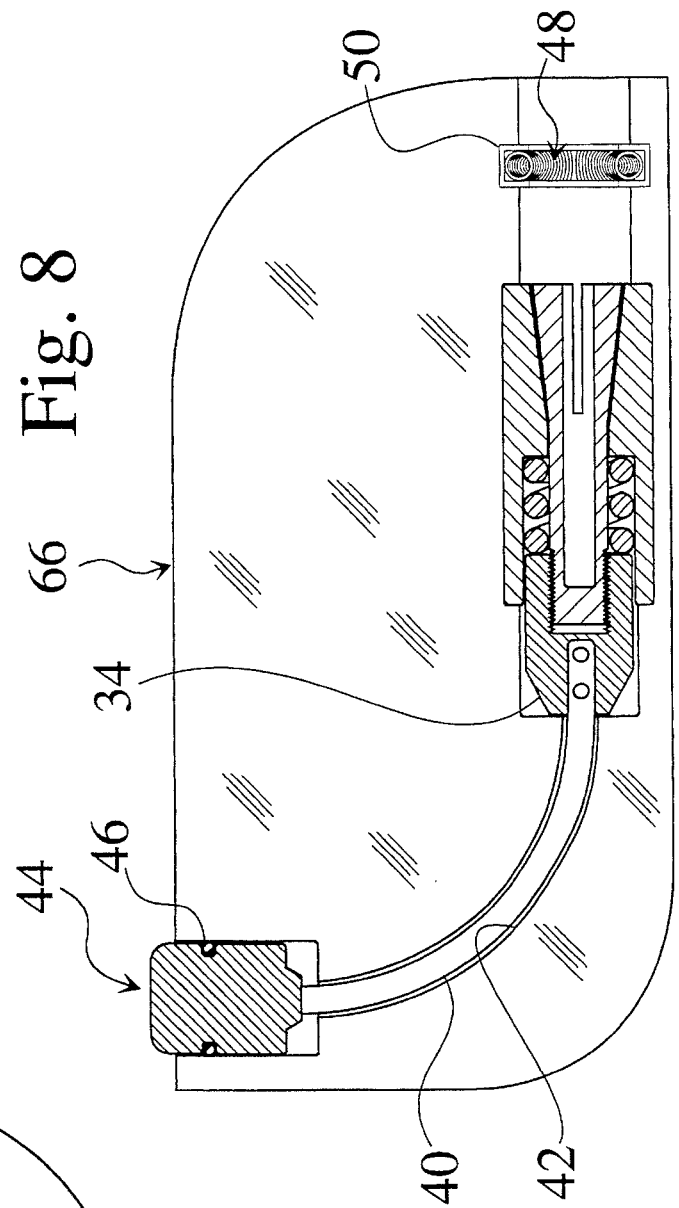

ELECTRICAL TERMINAL WITH A COLLET GRIP FOR A DEFIBRILLATOR

FIELD OF THE INVENTION

This invention relates generally to electrical terminals that are used for detachably connecting electrical leads to electrical devices, and more specifically to lead connectors for use with implantable defibrillators and pacemakers.

BACKGROUND OF THE INVENTION

The operation of an implantable heart defibrillator requires the transmission of low level electrical signals generated by the heart to the defibrillator, as well as the pacing and defibrillation currents generated by the defibrillator to the heart. This physical link of transmission, the pacemaker or defibrillator lead, is a section of fatigue-resistant, insulated electrical conductor designed to endure the severe environment inside the human body. Any leakage of body fluids to the conductor can result in deterioration of the signals transmitted, due to corrosion of the conductor or connections, or to the creation of a current leakage path. The distal end of the lead, in the form of an electrode, provides conduction to the tissue. The proximal end of the lead in the form of a lead connector pin, is connected to the terminal of the defibrillator. The materials used to construct the pacemaker or defibrillator lead must be biocompatible. For insulation, common selections are silicone rubber and polyurethane. For the conductors, common selections are titanium and its alloys, 316L stainless steel, MP35N, silver composites, and platinum and its alloys.

Conventional pacemakers and defibrillators require a set screw to secure the lead connector pin to the terminal. A molded silicone rubber, thermoplastic, or epoxy top, or header, is used to encapsulate the terminal, leaving an opening, or connector cavity, for the lead connector pin to be inserted through. A small, self-sealing slit is cut in the silicone rubber top above the terminal to allow a wrench, such as an allen wrench, to gain access to the set screw. Alternatively, for an epoxy header, an additional opening is provided to the set screw, which is later sealed by application of silicone adhesive or a sealing cap screw. The set screw design provides good mechanical locking of the lead connector pin, along with electrical continuity between the lead connector pin and the terminal. A sealing mechanism on the lead connector located distal to the lead connector pin is used to prevent body fluids from contacting the lead connector pin and metal components of the terminal through the connector cavity.

During an implant operation, the surgeon is required to locate the external opening in the top, insert the wrench to engage the set screw, and apply the appropriate torque to tighten the set screw. There is a chance that the silicone rubber top or the self-sealing slit might become damaged and fail to provide adequate sealing, or that the cap screw or silicone adhesive may be inadvertently omitted or misapplied, thereby allowing body fluids to penetrate through to the terminal. This may result in deterioration of the heart signals, current shunting from the terminal to the subcutaneous tissue at the defibrillator generator implant site, and corrosion of the terminal and the lead connector pin. Even when properly applied, these extra sealing mechanisms required to cover the wrench entrance may be leaky over the life of the defibrillator.

The defibrillator is battery operated and therefore requires replacement every few years. However, the lead is still functional, and remains in place in the body. To replace the defibrillator, the set screw must be loosened to remove the lead. If the set screw, terminal, or lead connector pin has corroded, this may be impossible without damaging the lead.

Set screws and the wrenches required to use them are very small, are often supplied loose, and are difficult to handle with gloves. When used in the operating room, there is danger of their being dropped either outside the sterile field, or into the open wound of a patient where they may be difficult to retrieve.

An additional problem with prior art systems is that lead connector pins are often provided with a through hole for inserting a stylet to stiffen the lead to facilitate placement in the body. In that case, a set screw can collapse the wall of the pin, due to its point contact, deforming the pin and making it difficult to remove, or making it impossible to reinsert the stylet if necessary to move the lead. Such deformation is also undesirable since it could result in offset of the lead connector with respect to the connector cavity, resulting in poor sealing of the lead sealing mechanism. However, with a design using a balanced radial force on the lead connector pin, these problems would be minimized or eliminated.

New generation pacemakers and defibrillators require the terminals to be more compact in size and more robust in their use. The existing set screw design, limited by the use of a wrench and a threaded hole configuration, has been found to be inadequate not only with regard to compactness, but also with respect to ease of operation.

U.S. Pat. No. 5,069,209 to Posin describes a collet grip system, which eliminates the need for a set screw and other extra tools. This system uses a camming device to open and close the collet. The cams must be squeezed between the forefinger and thumb through the insulating header material. Therefore, this material is limited to a flexible material like silicone rubber. Also, current defibrillators typically have three or more lead connector cavities to accommodate at least two defibrillator leads and one pacing and sensing lead. The invention of Posin would not allow for side by side placement of the connector cavities, and would therefore require that the cavities be stacked to form an unusually tall header.

U.S. Pat. No. 4,540,236 to Peers-Trevarton describes a connector with a locking and releasing mechanism having gripping members for gripping a pacing lead connector pin having a specially formed groove. While the invention allows for easy locking and removal of a lead, the lead must be one having the special groove. Because few leads that are implanted have such a feature, the device would have limited use in the pulse generator replacement market. Also, two new international standards, ISO 5841-3, "Cardiac pacemakers—Part 3: Low-profile connectors (IS-1) for implantable pacemakers", and ISO 11318, "Cardiac defibrillators—Connector assembly for implantable defibrillators—Dimensional and test requirements", are approved industry standards. These standards specify a standard pacing and defibrillation connector assembly to allow leads and pulse generators from different manufacturers to be interchangeable. While it may be possible to use the invention of Peers-Trevarton to make a lead connector cavity conforming to the standards, the invention would not allow for the lead connector to conform to the standard, since there is neither a groove nor room for a groove on the pin in the standard. Since the lead connector cavity would require a lead with a groove in its connector pin, interchangeability with standard-conforming leads would be impossible.

U.S. Pat. No. 4,784,141 to Peers-Trevarton describes another lead locking mechanism which uses a compression ring instead of a collet or set screw to make contact with the lead connector pin. In this invention, the ring is tightened onto the pin by bearing down on it with a screw using a screw driver. The screw is sealed from the rest of the terminal by means of an o-ring that rotates and slides on the surface of a counterbore in the header.

SUMMARY OF THE INVENTION

Briefly stated, and in accordance with one embodiment of the invention, there is provided a terminal for detachably connecting an electrical lead to an electrical device. The terminal includes an outer sleeve adapted to be fixed and electrically attached to the device. The terminal further includes a movable collet adapted to be carried by the outer sleeve for movement between first and second positions relative to the outer sleeve. The collet includes at least two fingers thereon movable relatively toward and away from one another between a first spaced apart position less than the diameter of the lead connector pin and a second spaced apart position greater than the diameter of the lead connector pin, for receiving and releasing the lead connector pin in the second spaced apart position, and for gripping the lead connector pin in the first spaced apart position. The terminal further includes push button means for moving the movable collet from its first to its second position; and a compression spring for moving the movable collet from its second to its first position.

A primary object of the invention, therefore, is to provide an improved terminal for effortless, positive and secure mechanical and electrical connection of an electrical lead to an electrical device, for example an implantable heart defibrillator.

A further object of the invention is to provide an improved terminal for effortless, simple and reliable disconnection of the electrical lead from the electrical device, when required.

Another object of the invention is to provide an improved defibrillator terminal which eliminates the need for the use of any special tools for connecting and disconnecting a lead connector to a defibrillator terminal.

Another object of the invention is to provide a terminal which has no loose parts which could be lost or incorrectly installed.

A still further object of the invention is to prevent body fluids from penetrating into a defibrillator terminal through wrench openings in the insulative top of a defibrillator case.

Another object of the invention is to provide a terminal which can be made to comply with existing industry standards, for interchangeability.

Yet another object of the invention is to provide a reduction in the size of the defibrillator terminal, and in the overall dimensions of the insulative top.

BRIEF DESCRIPTION OF THE DRAWINGS

The various features and advantages of the present invention may be more readily understood with reference to the following detailed description taken in conjunction with the accompanying drawings where like reference numerals are used to designate like elements and in which:

FIGS. 6A and 6B show alternate embodiments of the collet;

FIG. 7 is a view of an optional hexagonal configuration of the terminal; and

FIG. 8 is a cross-sectional view of a defibrillator with a collet grip with a remote push button for actuating the collet to grip or to release the lead connector pin.

DETAILED DESCRIPTION OF THE INVENTION

Figure 1:
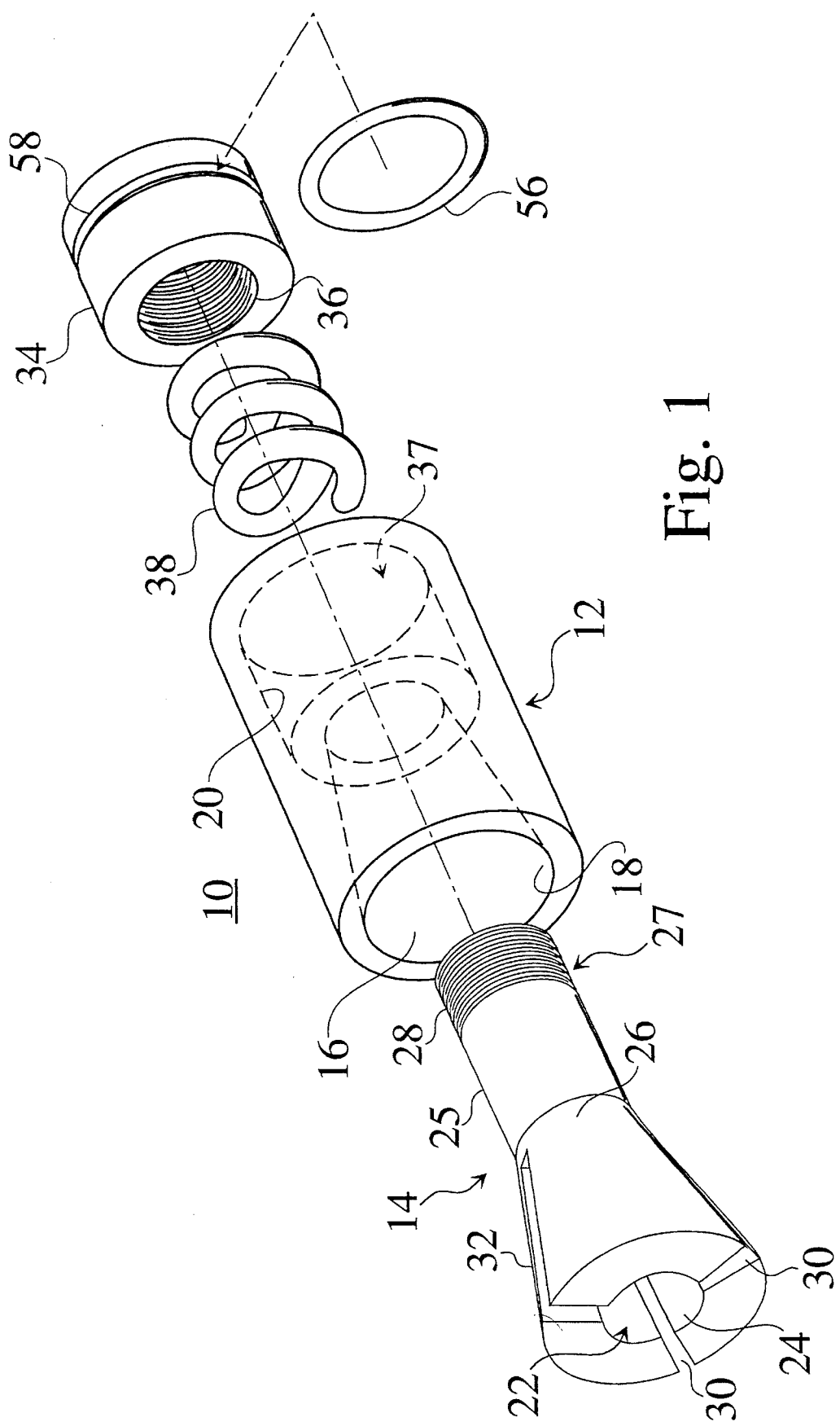
FIG. 1 is an exploded perspective of the terminal of the invention.

FIG. 1 shows an exploded view of a terminal 10 in accordance with the invention, for use with an implantable heart defibrillator (not shown). The terminal 10 includes a generally cylindrical outer sleeve 12 and a collet member 14. The outer sleeve 12 is fabricated out of biocompatible, non corrosive metal such as titanium, MP35N, or 316L stainless steel. A through hole or aperture 16 is formed in the outer sleeve 12, with a tapered portion 18 that flares out to a larger diameter at the entrance portion thereof and a straight bore portion 20 at the exit thereof.

Collet member 14 is provided with an elongate aperture 22, with an entrance end 24, which may be a through hole or a blind hole. In the case where aperture 22 is a blind hole, the bottom of the hole may serve as a stop for the lead connector pin, provided the hole is shallower than the length of the pin. Aperture 22 is made to be just slightly larger in diameter than the diameter of the connector pin of the lead that is to be received therein, so that the lead connector pin can be inserted and removed conveniently when the collet 14 is in its radially expanded, relaxed condition.

Entrance end 24 of aperture 22 is followed by a tapered portion 26, which necks down to a middle portion 25 having a smaller diameter than the outer diameter of the entrance end 24. At the opposite end of collet member 14, straight threads 28 are provided on a base portion 27. In addition, three longitudinal slots 30 are cut into tapered portion 26 of the collet member 14. The slots 30 extend from the end 24 to the generally cylindrical middle portion 25 to transform a portion of the annular wall of the collet member into three radially movable fingers 32.

Terminal 10 is also provided with a release member 34, which is fabricated from an insulative, biocompatible material such as acetal or ultra high molecular weight polyethylene (UHMWPE). Release member 34 is formed in a cup shape that includes a threaded straight portion 36. The threaded portion 36 is adapted to mate with the threads 28 of collet 14. Alternatively, threads 28 and 36 may be replaced by a different mating mechanism, such as glue, locking pins, a leaf spring in a groove, and so forth.

Terminal 10 is also provided with a spring 38. The spring is preferably in the form of a cylindrical coil and is fabricated from biocompatible metal. Spring 38 is employed to provide a compressive spring force for moving collet member 14 within aperture 16 of outer sleeve 12, as will be described in greater detail hereinafter. An o-ring seal 56 fits in an o-ring groove 58 on release member 34.

The design of terminal 10 requires the assembly of the components to be performed in a particular sequence. First, collet member 14 is inserted in aperture 16 in outer sleeve 12. Then, spring 38 is installed on to the outside surface of the collet member 14 on the middle portion 25 by sliding it into straight bore portion 20 and over the base portion 27 of the collet member 14. Next, the collet member 14, with the spring 38 positioned over the middle portion 25 thereof, is pushed further through aperture 16 in outer sleeve 12 sufficiently for the end of base portion 27 to project just slightly beyond the exit portion 37 of the outer sleeve 12. The release member 34 is then installed on to the threaded portion 28 of the collet member 14 by engaging the threads 36 of release member 34, then screwing the release member onto the collet member. This in turn pulls the collet 14 further into the tapered portion 18 of the outer sleeve 12 and compresses the fingers 32. By using threads 28 and 36 as the mating mechanism, adjustability is provided to position the collet 14 as desired, for example, to accommodate different connector pin sizes, or to set desired forces on the connector pin. The threaded design provides an additional advantage to the manufacturer by allowing various collets 14 for use with various sized connector pins to be interchangeable into terminal 10 without having to change any other parts. The threads 28 and 36 are shown as external and internal, respectively; they may, however, be internal and external, respectively. As mentioned previously, however, the mating mechanism is not limited to threads.

Figure 2:
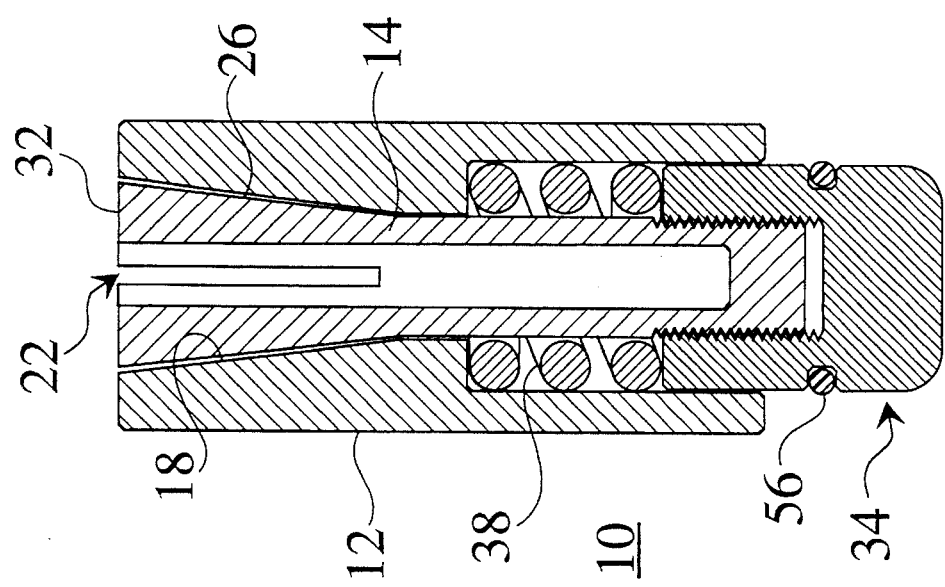
FIG. 2 is a cross-sectional view of the terminal shown in FIG. 1 as assembled.

FIG. 2 shows the completed assembly of terminal 10, with collet member 14 sitting in outer sleeve 12 with release member 34. In addition, spring 38 is under partial compression between the outer sleeve 12 and the release member 34. In the final assembly of terminal 10, the terminal is positioned inside the cavity of a header of insulative material, preferably a biocompatible epoxy or silicone rubber.

In FIG. 2, the lead connector pin has not yet been inserted into the assembled terminal 10. The spring 38 is slightly compressed and pushes the movable release member 34 outwardly of outer sleeve 12, pulling collet member 14 further into outer sleeve 12, so that the tapered portion 26 of the collet member 14 engages the tapered portion 18 of the stationary outer sleeve 12. The tapered surfaces 26 and 18 engage with one another during the movement of the movable collet member 14 and, thus, the fingers 32 are compressed radially inwardly by the tapered surface 18 acting against the tapered surface 26 during such movement. The inward compression of movable fingers 32 causes a reduction of the hole diameter during that movement. In the absence of a lead connector pin in the opening 22, the resulting diameter of the opening is reduced to a dimension that is less than the diameter of the lead connector pin. This position, and a position closely approaching it, wherein the movement of the collet 14 is limited by the abutment of the fingers 32 against the outer perimeter of an inserted lead connector pin, are hereinafter referred to as the "first position" of the movable collet member 14. Thus the spring 38 serves as a means in engagement with both the movable collet structure 14 and the stationary outer sleeve 12 for biasing the movable structure toward its first position.

Figure 3:
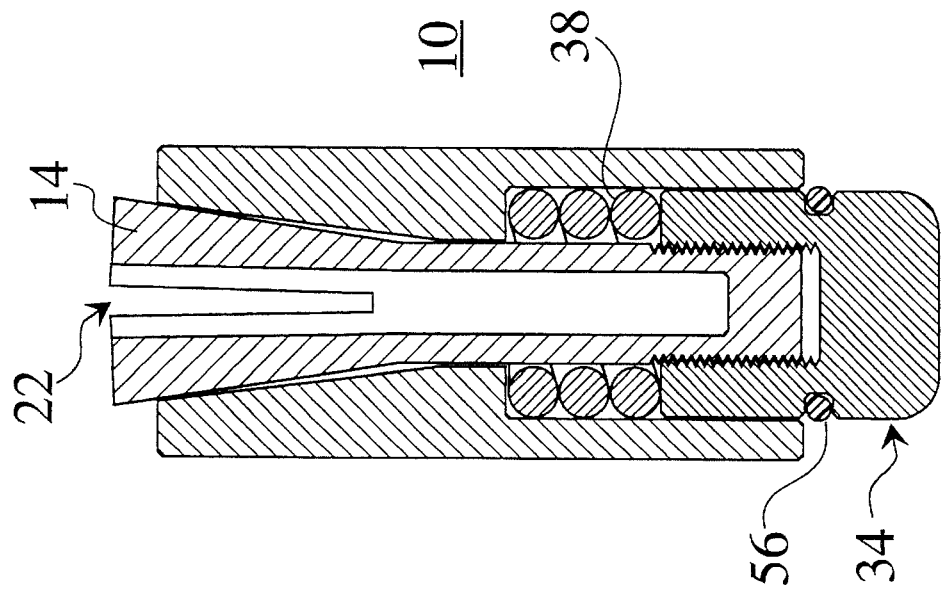
FIG. 3 is a view similar to FIG. 2, with the release means actuated to open the collet to facilitate insertion of a lead connector pin.

FIG. 3 shows the terminal 10 with release means 34 actuated. In order to connect the lead connector pin to terminal 10, release member 34 is pushed using finger pressure, compressing the spring 38. This position of the collet member 14 is hereinafter referred to as the "second position" of the movable collet 14. This action also moves the collet 14 to its second position.

Concurrently, the lead connector pin is inserted through an opening in the header, into the aperture 22 of collet member 14. Because there is sufficient clearance between the lead connector pin and the aperture 22, no interference occurs during the entry of the lead connector pin into the aperture 22 of collet member 14.

The insulative header material may be translucent, in which case the lead connector pin may be viewed through the header. A marking or other feature may be provided on the lead connector pin so that the surgeon stops inserting the lead at the desired location, then releases pressure on the release member 34.

Figure 4:
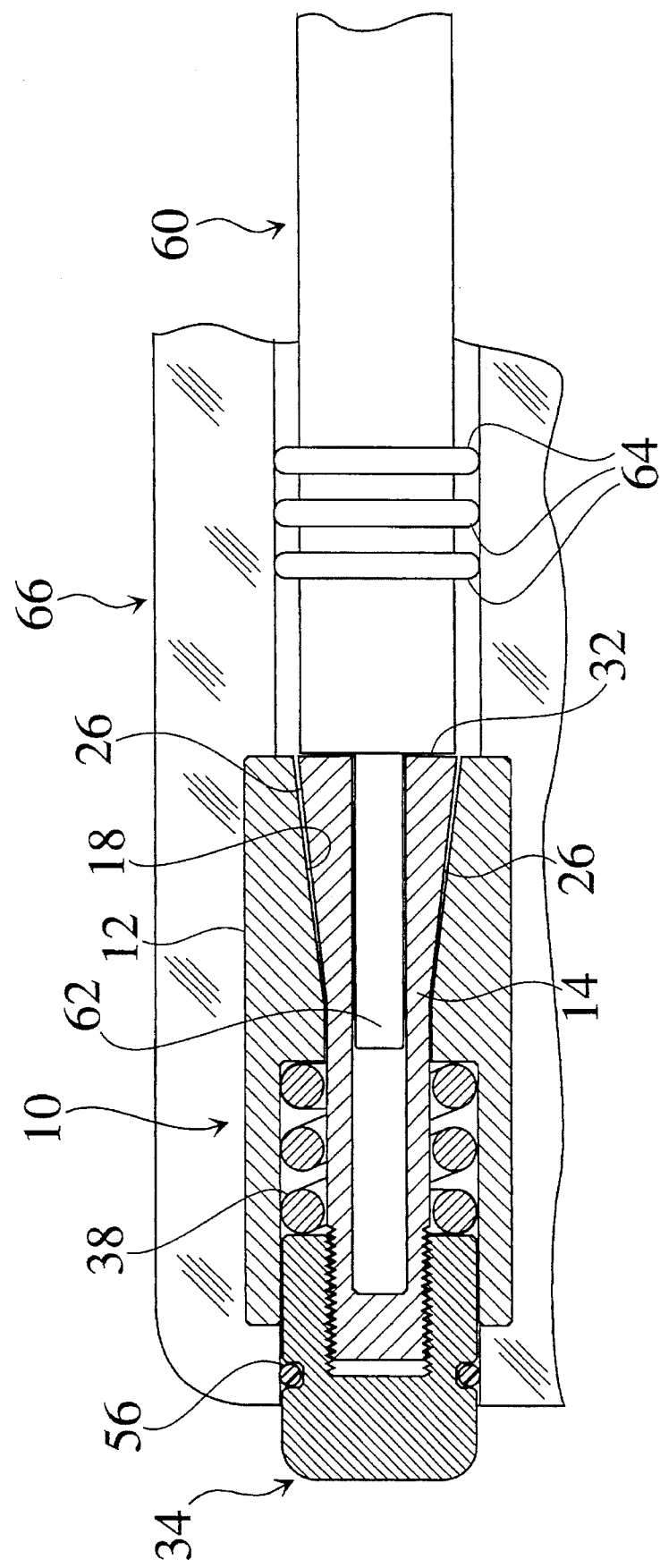
FIG. 4 is a view similar to FIG. 2, with the connector pin of an electrical lead inserted into, and being gripped by the terminal, and the terminal encapsulated inside an insulative header material.

FIG. 4 shows terminal 10 positioned in a header 66 with a lead connector pin 62 inserted and being gripped by the terminal. The metal-to-metal connector contact between the lead connector pin 62 and the collet member 14 is maintained due to the bias of spring 38 as spring 38 attempts to return to its fully-expanded position, pushing collet member 14 towards its first position and more fully re-engaging the tapered surfaces 18 and 26 of the outer sleeve 12 and collet member 14, respectively. The movable fingers 32 on the collet member 14 are thus squeezed to a closed position, and the release member 34 is pushed outward. At this stage, with the collet member 14 back to its first position, the lead connector pin 62 is fully locked up in terminal 10, and electrical continuity is fully established between the lead connector pin 62 and terminal 10.

O-ring seal 56 in o-ring groove 58 on release member 34 mates with a cavity in header 66 and prevents body fluids from entering the terminal 10 from the release member end. From the connector cavity end of header 66, the sealing mechanism 64 on the lead connector 60 prevents body fluids from entering the terminal 10.

Preferably, the angle used on the inner surface of the fingers 32 is chosen such that the static frictional force generated is always higher than any external pulling force likely to be encountered following implantation in the body. This assures that the lead connector pin 62 remains securely fastened to the terminal.

Figure 5:
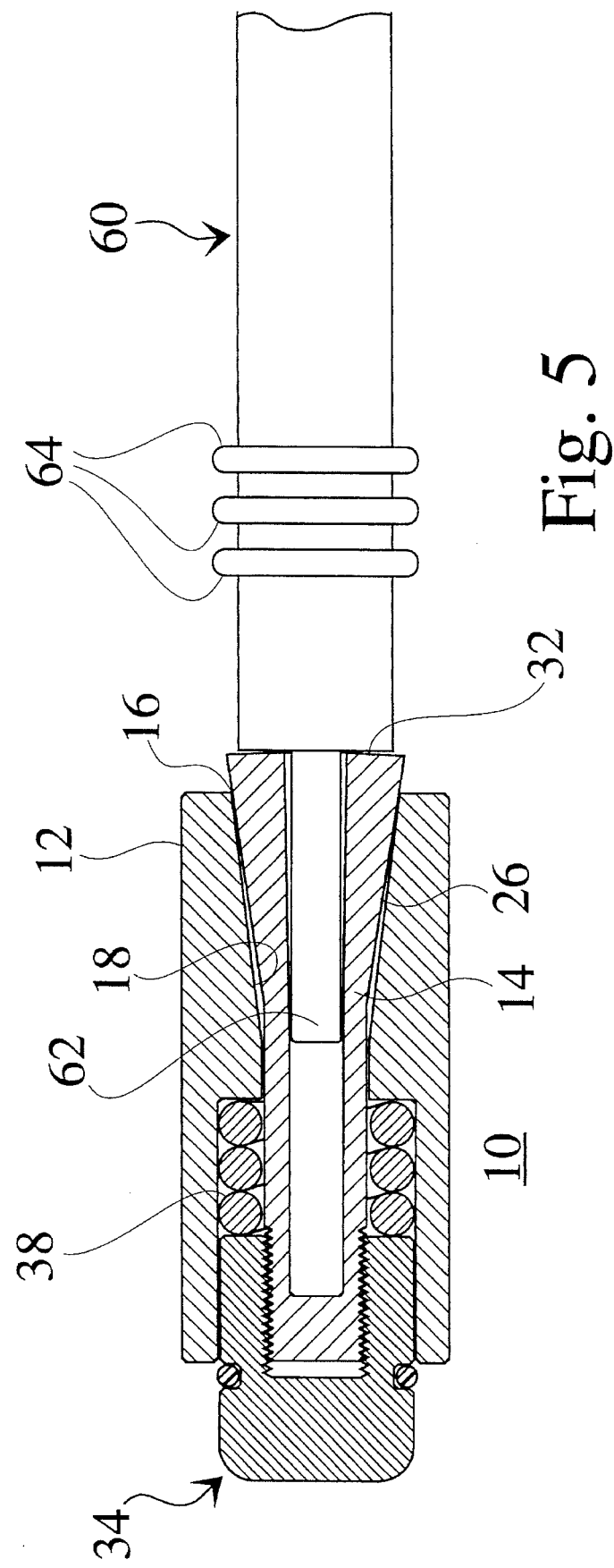
FIG. 5 is a view similar to FIG. 3, with the release means actuated to release is grip on the connector pin of the electrical lead in order to facilitate withdrawal of the lead from the terminal.

FIG. 5 shows the terminal 10 with release means 34 actuated to release its grip on the lead connector pin 62 to facilitate withdrawal. As indicated earlier herein, when it is time to disconnect the electrode lead connector 60 from terminal 10, a force is applied to the release member 34. The force compresses the spring 38, pushing the collet member 14 out of hole 16 in outer sleeve 12. This disengages the tapered surfaces 18 and 26 from one another, causing the fingers 32 on collet member 14 to spring open and disengage the lead connector pin 62. At this stage, the lead connector pin 62 can be gently pulled out and disconnected from the terminal 10.

FIG. 6A shows an alternate embodiment of the collet member 14. A collet ring 39 is provided to enhance the gripping characteristics relative to the connector pin of the electrical lead. Collet ring 39 may be located internal to and anywhere along the length of the tapered portion 26 of the collet 14. Collet member 14 or collet ring 39 may be provided with knurling, internal threads, or the like to roughen the interior surface thereof to increase the gripping characteristics of the collet 14 or collet ring 39. In this figure, aperture 22 is shown as a blind hole that is shallower than the length of connector pin 62. When the lead is fully inserted, pin 62 is bottomed in the blind hole 22.

FIG. 6B shows another embodiment of collet member 14. Another feature, such as recessed ring 52, is included on the inner faces of fingers 32 to engage with a feature on the lead connector pin 62, such as the raised ring 54 shown. The lead connector pin feature could be, as another example, a recessed ring around the pin for engagement with another kind of feature on the inner face of the collet fingers.

FIG. 7 is an end view of a hexagonal configuration of the terminal 10. The cross section of the inner surface 18 of the outer sleeve 12 and of the outer surface of the tapered portion 26 of collet 14 may be circular or noncircular. In this case where the surfaces are hexagonal, the collet 14 is prevented from rotating with respect to the outer sleeve 12. This ensures that the lead will not rotate within the header, and that the push button release member and its o-ring seal will not rotate within the header; therefore, all sealing rings within the connector system will see only pure translation following implantation.

FIG. 8 is a cross-sectional view of a collet grip with a remote push button for actuating the collet to grip or to release the lead connector pin. Release member 34 is connected to one end of a pushing element 40. Pushing element 40 runs through pushing element channel 42 in the header, and is connected to a push button 44 at its other end. An o-ring seal 46 prevents body fluids from entering through the header into the pushing element channel and in to the rest of the terminal. This remote push button configuration allows the manufacturer the design flexibility to place the push button in strategic locations.

FIG. 8 also shows a garter spring 48 in a garter spring channel 50 to provide electrical connection of a lead connector ring on bipolar connectors. The main mechanical connection would be provided by terminal 10 as discussed, but electrical connection would be provided by both terminal 10 and garter spring 48. Note that any number of garter spring connections could be provided and that they could be used with any configuration of terminal 10. Also, the garter spring could be replaced by a leaf spring or any other suitable spring.

It will be apparent from the foregoing description that the terminal of the invention provides for the effortless, simple and reliable connection to it, and disconnection from it, of an electrical lead connector. When used as a defibrillator terminal, the invention eliminates the need for any special tools or set screws, for connecting and disconnecting the lead connector pin to the pacemaker or defibrillator terminal. In addition, the elimination of wrench openings in the insulative header material facilitates the prevention of body fluids from penetrating into the pacemaker or defibrillator terminal. The design could be used with any header material, either flexible or rigid. Also, the improved terminal of the present invention provides for a reduction in the size of a pacemaker or defibrillator terminal, and in the overall dimensions of the header.

The invention has been described herein in connection with its use as a pacemaker or defibrillator terminal for connecting and releasing by hand pressure a lead connector to an implantable heart defibrillator. However, it will be apparent to those skilled in the art that the invention has broader applicability to electrical terminals generally, irrespective of the device to which the lead is to be connected. It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. A terminal for detachably connecting an electrical lead connector pin to an electrical device, comprising:

an outer sleeve adapted to be mechanically fixed and electrically connected to said device;

a collet structure adapted to be carried by said outer sleeve for movement between first and second positions relative to said outer sleeve, said collet structure having at least two fingers thereon movable relatively toward and away from one another between a first spaced apart position less than the diameter of said electrical lead connector pin and a second spaced apart position greater than the diameter of said electrical lead connector pin for gripping said lead connector pin in substantially said first spaced apart position and receiving and releasing said lead connector pin in said second spaced apart position;

push button positioning means for moving said collet from said first position to said second position, thus moving said fingers from said first spaced apart position to said second spaced apart position;

spring positioning means for moving said collet from said second position to said first position, thus moving said fingers from said second spaced apart position to first spaced apart position;

wherein said collet has a tapered outer surface portion, said outer sleeve has a tapered inner surface portion, and said collet tapered outer surface portion is in sliding contact with said outer sleeve tapered inner surface portion; and wherein the cross sections of said outer sleeve tapered inner surface portion and of said collet tapered outer surface portion are noncircular to prevent rotation of said collet with respect to said outer sleeve.

2. The terminal of claim 1 wherein said collet structure contains a blind hole having a bottom located at a depth that is less than or equal to the length of said lead connector pin, and wherein said lead connector pin stops against said bottom upon insertion of said lead connector pin into said blind hole.

3. The terminal of claim 1 wherein said cross sections are hexagonal.

4. The terminal of claim 1 wherein said electrical lead connector pin has an indented feature and wherein the inner surfaces of said fingers on said collet have a protruding feature to engage with said indented feature on said lead connector pin.

5. The terminal of claim 1 wherein said electrical lead connector pin has a protruding feature and wherein the inner surfaces of said fingers on said collet have an indented feature to engage with said protruding feature on said lead connector pin.

6. An implantable defibrillator including a pulse generator housing and a header coupled to said housing, said header including a spring contact supported within said header and a terminal for detachably connecting one or more leads each having one or more lead connector pins to said defibrillator, said terminal comprising:

an outer sleeve adapted to be mechanically fixed and electrically connected to said implantable defibrillator;

a collet structure adapted to be carried by said outer sleeve for movement between first and second positions relative to said outer sleeve, said collet structure having at least two fingers thereon movable relatively toward and away from one another between a first spaced apart position less than the diameter of said electrical lead connector pin and a second spaced apart position greater than the diameter of said electrical lead connector pin for gripping said lead connector pin in substantially said first spaced apart position and receiving and releasing said lead connector pin in said second spaced apart position;

push button positioning means for moving said collet from said first position to said second position, thus moving said fingers from said first spaced apart position to said second spaced apart position; and spring positioning means for moving said collet from said second position to said first position, thus moving said fingers from said second spaced apart position to first spaced apart position;

wherein said collet has a tapered outer surface portion, said outer sleeve has a tapered inner surface portion, and said collet tapered outer surface portion is in sliding contact with said outer sleeve tapered inner surface portion;

wherein the cross sections of said outer sleeve tapered inner surface portion and of said collet tapered outer surface portion are noncircular to prevent rotation of said collet with respect to said outer sleeve; and wherein when said terminal receives a bipolar lead having a connector pin and a connector ring said connector pin is received in said collet structure and said connector ring is engaged by said spring contact.

7. The implantable defibrillator of claim 6 wherein the number of said fingers is three.

8. The implantable defibrillator of claim 6 wherein said collet is attached by threads to said push button positioning means for moving said collet from said second position to said first position and for moving said fingers from said second spaced apart position to first spaced apart position.

9. The implantable defibrillator of claim 6, and further including a sealing mechanism located on said push button positioning means to prevent fluid from contacting said lead connector pin.

10. The implantable defibrillator of claim 6 wherein said spring positioning means is a circular compression spring.

11. The implantable defibrillator of claim 6, wherein said push button positioning means comprises:

a push button positioned at a location which is accessible for pressing with a finger;

a pushing element channel;

a pushing element residing within said pushing element channel; and a release member, said release member being mechanically attached to said push button by said pushing element such that substantially the force of depressing said push button is transferred to said release member, causing said collet to move from said first position to said second position, thus moving said fingers from said first spaced apart position to said second spaced apart position.

12. The implantable defibrillator of claim 6 wherein said spring is a garter spring.

13. The implantable defibrillator of claim 6 wherein said collet structure contains a blind hole having a bottom located at a depth that is less than or equal to the length of said lead connector pin, and wherein said lead connector pin stops against said bottom upon insertion of said lead connector pin into said blind hole.

14. The implantable defibrillator of claim 6 wherein said collet has a tapered outer surface portion, said outer sleeve has a tapered inner surface portion, and said collet tapered outer surface portion is in sliding contact with said outer sleeve tapered inner surface portion.

15. The implantable defibrillator of claim 14 wherein the cross sections of said outer sleeve tapered inner surface portion and of said collet tapered outer surface portion are noncircular to prevent rotation of said collet with respect to said outer sleeve.

16. The implantable defibrillator of claim 15 wherein said cross sections are hexagonal.

17. The implantable defibrillator of claim 6 wherein the inner surfaces of said fingers on said collet have a protruding feature to engage with an indented feature on said lead connector pin.

18. The implantable defibrillator of claim 6 wherein the inner surfaces of said fingers on said collet have an indented feature to engage with a protruding feature on said lead connector pin.

* * * * *